(12) United States Patent
Mujwid

(10) Patent No.: US 7,935,135 B2
(45) Date of Patent: May 3, 2011

(54) SPINAL FIXATION DEVICE

(75) Inventor: James R. Mujwid, Crystal, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 884 days.

(21) Appl. No.: 10/865,672

(22) Filed: Jun. 9, 2004

(65) Prior Publication Data
US 2006/0089643 A1    Apr. 27, 2006

(51) Int. Cl.
*A61B 17/70* (2006.01)
(52) U.S. Cl. .......................... 606/266; 606/278
(58) Field of Classification Search .............. 606/61, 606/72–73, 246, 250–262, 264–279
See application file for complete search history.

(56) References Cited

U.S. PATENT DOCUMENTS

| | | | |
|---|---|---|---|
| 5,129,388 A | 7/1992 | Vignaud et al. | |
| 5,176,680 A * | 1/1993 | Vignaud et al. | 606/61 |
| 5,443,467 A | 8/1995 | Biedermann et al. | |
| 5,476,464 A | 12/1995 | Metz-Stavenhagen | |
| 5,628,740 A | 5/1997 | Mullane | |
| 5,672,176 A | 9/1997 | Biedermann et al. | |
| 5,728,097 A | 3/1998 | Mathews | |
| 5,733,286 A | 3/1998 | Errico et al. | |
| 5,735,850 A | 4/1998 | Baumgartner et al. | |
| 5,782,833 A * | 7/1998 | Haider | 606/61 |
| 5,879,350 A | 3/1999 | Sherman et al. | |
| 5,882,350 A | 3/1999 | Ralph et al. | |
| 6,050,997 A | 4/2000 | Mullane | |
| 6,053,917 A * | 4/2000 | Sherman et al. | 606/61 |
| 6,074,391 A | 6/2000 | Metz-Stavenhagen et al. | |
| 6,113,601 A | 9/2000 | Tatar | |
| 6,132,432 A | 10/2000 | Richelsoph | |
| 6,248,105 B1 | 6/2001 | Schlapfer et al. | |
| 6,273,888 B1 * | 8/2001 | Justis | 606/61 |
| 6,280,442 B1 * | 8/2001 | Barker et al. | 606/60 |
| 6,287,309 B1 | 9/2001 | Baccelli et al. | |
| 6,355,040 B1 | 3/2002 | Richelsoph et al. | |
| 6,371,957 B1 | 4/2002 | Amrein et al. | |
| 6,488,681 B2 | 12/2002 | Martin et al. | |
| 6,565,565 B1 * | 5/2003 | Yuan et al. | 606/61 |
| 7,066,937 B2 * | 6/2006 | Shluzas | 606/61 |
| 2003/0167058 A1 * | 9/2003 | Shluzas | 606/61 |

FOREIGN PATENT DOCUMENTS

DE    43 30 837 A1    3/1995

(Continued)

OTHER PUBLICATIONS

Centerpulse Spine-tech Inc. product specification sheet for Dynalok™ (New), © 2003, 2 pages.
Centerpulse Spine-tech Inc. product specification sheet for Dynalok™ (Old), © 2003, 2 pages.
Centerpulse Spine-tech Inc. product specification sheet for Monarch™, © 2003, 2 pages.
Centerpulse Spine-tech Inc. product specification sheet for Steffee™ Plate, © 2003, 2 pages.
DePuy AcroMed™ catalog for Monarch™ Spine System, no date provided, cover and p. 6.

(Continued)

*Primary Examiner* — Thomas C Barrett
*Assistant Examiner* — Michael J Araj
(74) *Attorney, Agent, or Firm* — Seager, Tufte & Wickhem, LLC

(57) ABSTRACT

A bone fixation device including a retainer and an anchor. The retainer includes first and second receiving regions. The first receiving region is configured for receipt of a connecting rod. The second receiving region is configured for receipt of an anchor. The first receiving region is constructed so that a connecting rod can be positioned within the receiving region at a number of non-coaxial orientations. The first receiving region is also constructed to accommodate a curved connecting rod. A flexible, integral locking structure is located between the first and second receiving regions. The locking structure is arranged to secure each of the retainer, an anchor, and a connecting rod in a position relative to one another.

37 Claims, 14 Drawing Sheets

FOREIGN PATENT DOCUMENTS

| | | |
|---|---|---|
| EP | 1 138 267 A2 | 10/2001 |
| EP | 1 335 675 B1 | 8/2003 |
| JP | 2000-325359 | 7/2000 |
| WO | WO 02/76315 A1 | 10/2002 |
| WO | WO 2004/032772 A2 | 4/2004 |

OTHER PUBLICATIONS

Medicrea® catalog for PASS MED™ Polyaxial Spine System, © Jan. 2002.

* cited by examiner

SPINAL FIXATION DEVICE

TECHNICAL FIELD

This disclosure relates generally to devices, and associated methods, for stabilizing spinal alignment. More particularly, this disclosure relates to a medical implant, such as a bone screw device configured to receive a connecting rod, and associated methods.

BACKGROUND

The human spinal column is prone to diseases or disorders that produce disruption of the normal alignment of the spine. Frequently, treatment of spinal disorders involves spinal stabilization, for example, by immobilization of the affected vertebral joint(s). One spinal stabilization technique includes a surgical process wherein implants are attached to the spinal vertebrae and connected with spinal rods. In particular, a combination of bone screw arrangements and connecting rods are used to provide a stabilizing construct secured to the spinal vertebrae for the purpose of stabilizing and/or adjusting spinal alignment.

FIG. 1 illustrates one conventional bone screw arrangement 1 for use with a connecting rod 7. The arrangement 1 includes an anchor 2, a yoke member 3, and an internal locking piece 4. The internal locking piece 4 has an outer tapered surface, and is positioned within a correspondingly tapered bore 5 of the yoke member 3.

In use, the connecting rod 7 is aligned with the yoke member 3 for placement of the connecting rod within the saddle of the yoke member 3. Because connecting rods are often times bent to correspond to the curvature of the patent's spinal structure, positioning the connecting rod within the saddle of the yoke member can be difficult.

Once the connecting rod 7 is properly positioned, a lock nut 6 is tightened down onto the yoke member 3. The lock nut 6 forces the connecting rod 7 into the saddle of the yoke member 3 and against the top of the locking piece 4, while at the same time, drawing the yoke member 3 upwardly relative to the locking piece 4 (see relative motion represented by arrows in the enlarged detail view). As the lock nut 6 draws the yoke member 3 upward, and forces the connecting rod 7 downward, the tapered arrangement of the yoke member 3 and the internal locking piece 4 causes the locking piece 4 to compress radially inward. Compression of the locking piece 4 causes the locking piece 4 to clamp on the head of the anchor 2 to fix the anchor 2 at a desired angular orientation relative to the yoke member 3. Concurrently, the rod 7 is clamped between the nut 6 and the top of the locking piece 4.

As can be understood, the size of a bone screw arrangement is an important aspect in minimizing the invasiveness of a surgical stabilization procedure. In the arrangement of FIG. 1, at least three components: the anchor 2, the yoke member 3, and the locking piece 4, functionally dictate the size of the arrangement.

In general, improvement has been sought with respect to such devices and arrangements, generally to better accommodate: manufacture and assembly, ease of use, reduced invasiveness, and, adaptability for a variety of spinal surgery applications.

SUMMARY

In one aspect, the present disclosure relates to a retainer for use with a bone anchor and a connecting rod. The retainer includes a body having a longitudinal axis defined between a first end and a second end. The body includes a first receiving region located adjacent to the first end, and a second receiving region located adjacent to the second end. The body further includes at least one flexible element positioned between the first receiving region and the second receiving region, the flexible element being configured to flex toward the second receiving region when a connecting rod is secure within the first receiving region.

Another aspect of the present disclosure relates to a retainer having a main body and first and second arms extending from the main body. The first and second arms define a central axis there between; the central axis being generally perpendicular to a longitudinal axis of the main body. The main body also includes a first receiving region located at the first end of the main body, and a second receiving region located at the second end of the main body. The first and second arms are configured to permit placement of a connecting rod within the first receiving region at a number of angular orientations relative to the central axis defined by the first and second arms.

Still another aspect of the present disclosure relates to a fixation device including a retainer, an anchor, and a securing member. The retainer includes a saddle region located at a first end and a socket located at a second end. A flexible intermediate structure is located between the saddle region and the socket. Each of the retainer, the anchor, and a connecting rod positioned with the saddle region of the retainer are secured in a fixed position relative to one another when the securing member seats the connecting rod within the saddle region.

Another aspect of the present disclosure relates to a retainer having a first receiving region configured to receive a connecting rod, and a second receiving region configured to receive a bone anchor. The first receiving region includes arms that define a central axis extending there between. The arms further defining a center dimension, a first lateral dimension, and a second lateral dimension. The center, first lateral, and second lateral dimensions are transverse to the central axis. The first and second lateral dimensions are greater than the center dimension.

Yet another aspect of the present disclosure relates to a bone fixation device including a yoke, a bone anchor, and a plurality of clamping member. The yoke has an upper pocket for receiving a connecting rod and a lower socket. The bone anchor has a head mounted in the lower socket of the yoke. The plurality of clamping members has upper surfaces that define a portion of the upper pocket and lower surfaces that define a portion of the lower socket. The clamping members are integrally connected with the yoke at flex locations, and are configured to clamp the head of the bone anchor within the lower socket when the connecting rod is secured within the upper pocket.

Still another aspect of the present disclosure relates to a method of using a bone screw arrangement. The method includes providing a bone screw arrangement having an anchor and a retainer including an integral locking structure. The method further includes positioning the anchor within a socket of the retainer, pivoting the anchor to a selected axial orientation relative to a longitudinal axis of the retainer, and positioning a connecting rod within a saddle region of the retainer at a non-coaxial orientation relative to a central axis of the retainer.

A variety of examples of desirable product features or methods are set forth in part in the description that follows, and in part will be apparent from the description, or may be learned by practicing various aspects of the disclosure. The aspects of the disclosure may relate to individual features as well as combinations of features. It is to be understood that both the foregoing general description and the following detailed description are explanatory only, and are not restrictive of the claimed invention.

DETAILED DESCRIPTION

Reference will now be made in detail to various features of the present disclosure that are illustrated in the accompanying drawings. Wherever possible, the same reference numbers will be used throughout the drawings to refer to the same or like parts.

FIGS. 2-14 illustrate a bone screw arrangement 10 in accord with the principles of the present disclosure. The bone screw arrangement 10 is designed for use with a connecting rod 50 in spinal stabilization surgeries. The bone screw arrangement 10 generally includes a yoke or retainer 12 and a bone anchor 14 (also known as an anchor or pedicle screw). The bone screw arrangement 10 is configured to secure each of the retainer 12, the connecting rod 50, and the anchor 14 in a position relative to one another.

Figure 2:
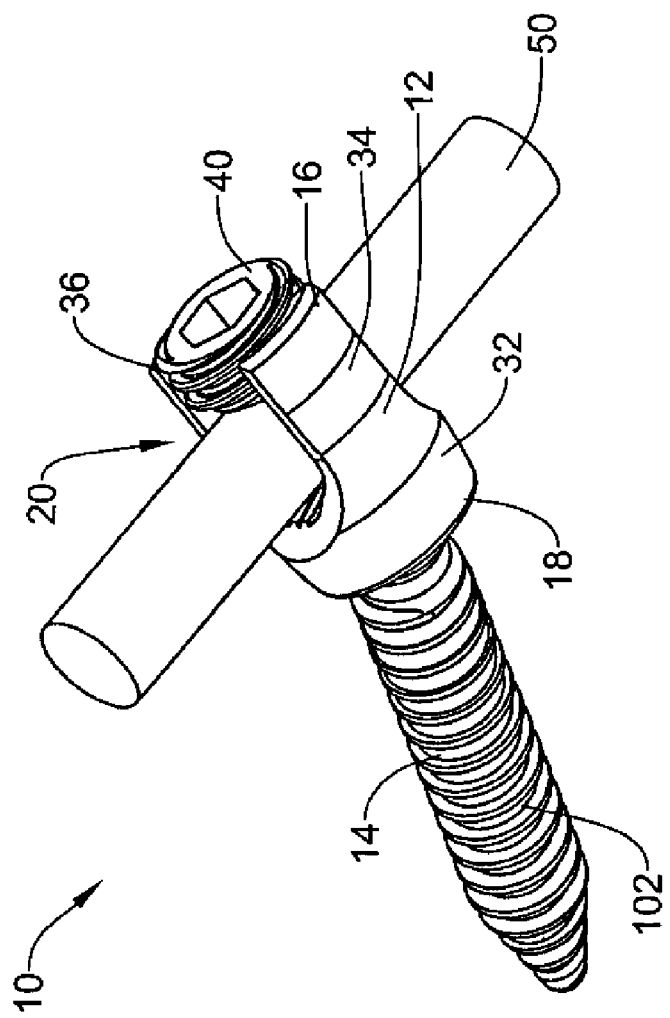
FIG. 2 is a perspective view of one embodiment of a bone screw arrangement, according to the principles of the present disclosure.
Figure 3:
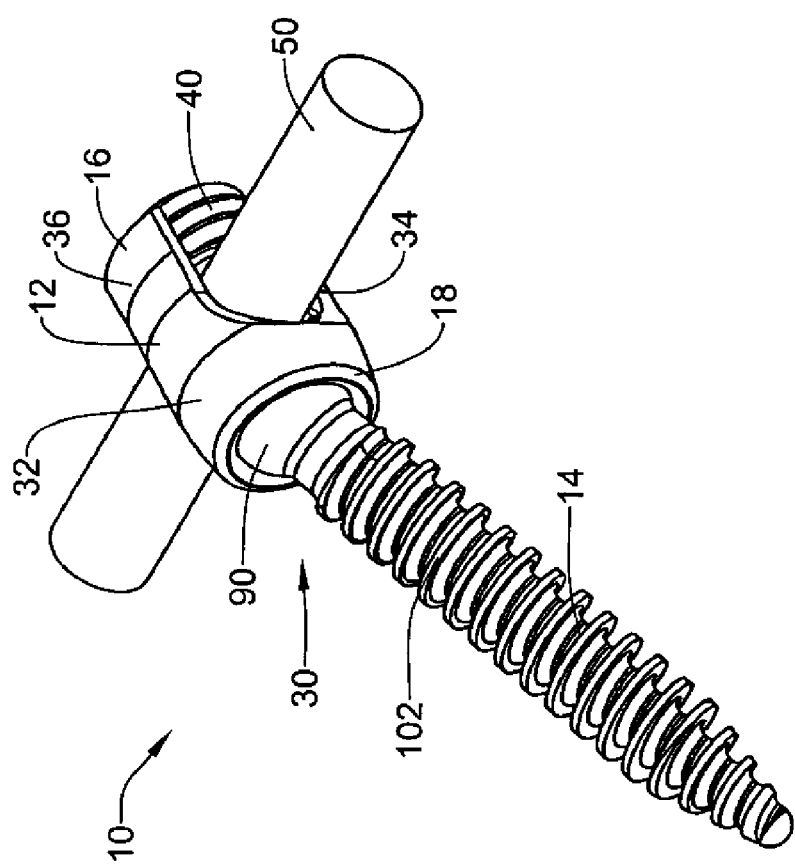
FIG. 3 is another perspective view of the bone screw arrangement of FIG. 2.
Figure 4:
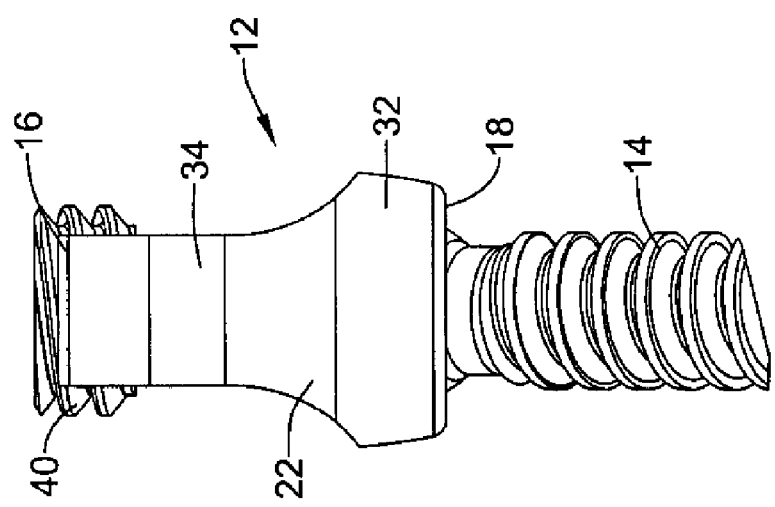
FIG. 4 is a partial side view of the bone screw arrangement of FIG. 2.

Referring to FIGS. 2-4, the retainer 12 generally includes a retainer body 22 having a first receiving region 20 located adjacent to a first end 16 of the retainer body 22, and a second receiving region 30 located adjacent to a second end 18 of the retainer body 22. The first receiving region 20 (also referred to as a saddle or pocket) is configured to receive a connecting rod 50. The second receiving region 30 is configured to receive a head 90 of the anchor 14. In the illustrated embodiment, the retainer body 22 includes a main body portion 32 and first and second arms 34, 36 that extend outward from the main body portion 32.

Figure 8:
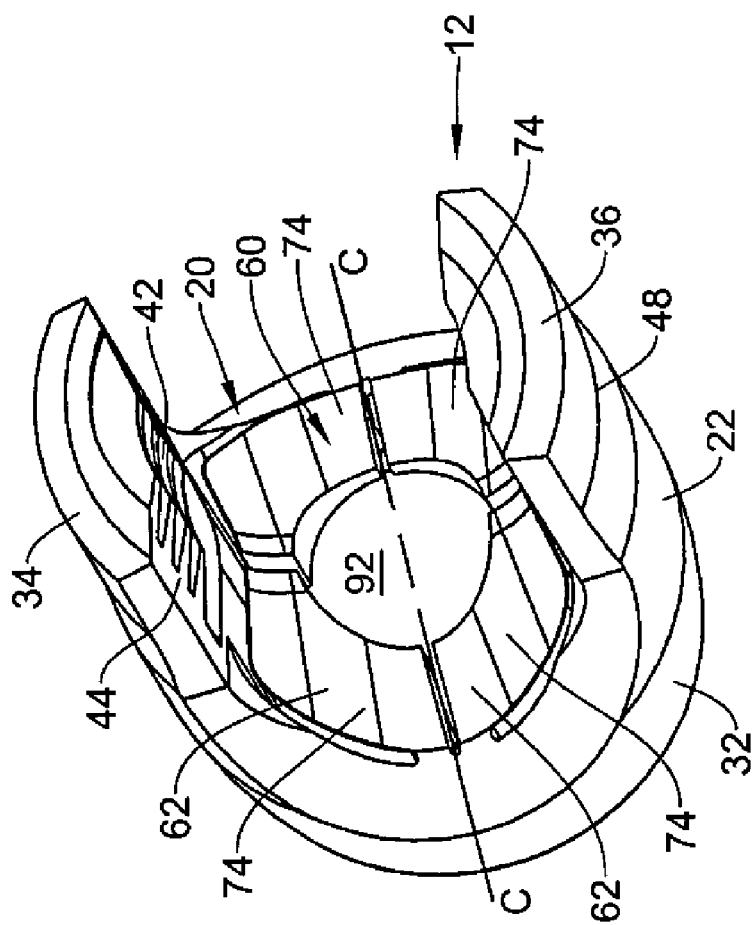
FIG. 8 is a top perspective view of the retainer of FIG. 5.

Referring now to FIGS. 5-8, the arms 34, 36 of the retainer body 22 extend parallel with a longitudinal axis A-A (FIG. 6) that runs from the first end 16 of the retainer body 22 to the second end 18 of the retainer body. The retainer body 22 also includes intermediate structure 60 (FIG. 8). The top side of the intermediate structure 60 and the first and second arms 34, 36 define the first receiving region 20 within which the connecting rod 50 is placed. The bottom side of the intermediate structure 60 and the main body portion 32 define the second receiving region 30 within which the head 90 of the anchor 14 is positioned.

Figure 5:
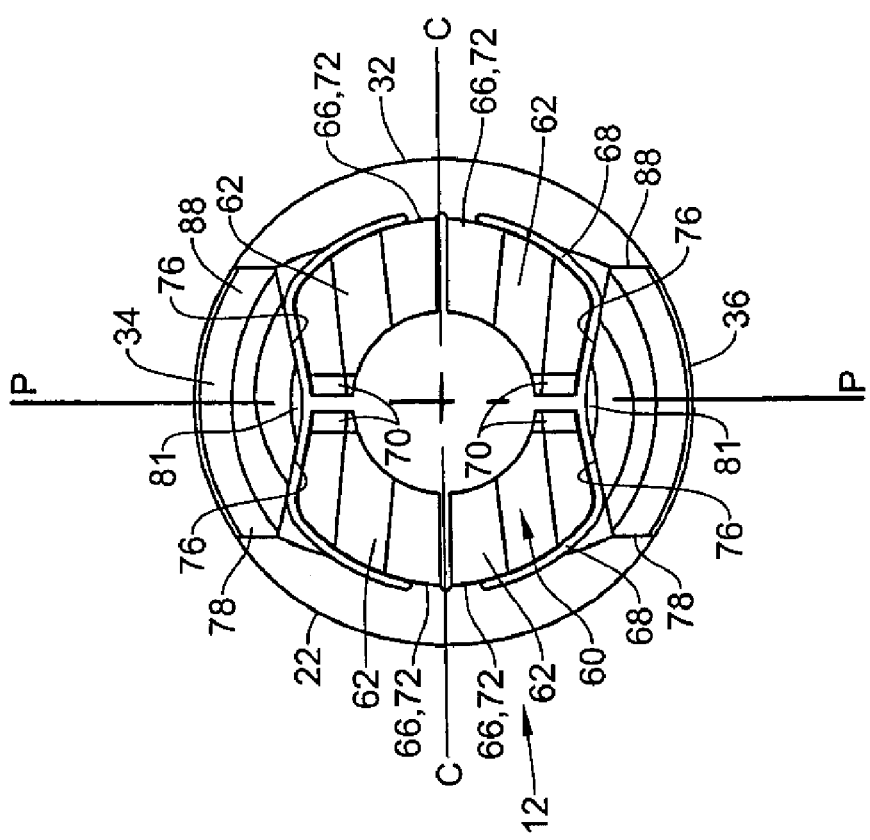
FIG. 5 is a top plan view of one embodiment of a retainer of the bone screw arrangement of FIG. 2.

As shown in FIGS. 5 and 8, the first and second arms 34, 36 include inner surfaces 44, 46 oriented in an opposed relationship to one another. A central axis C-C is defined between the first and second arms 34, 36, and bisects the first receiving region 20. The central axis C-C is generally perpendicular to the longitudinal axis A-A of the retainer body 22.

The inner surfaces 44, 46 of the arms 34, 36 include angled faces 76 (FIG. 5) that extend in a non-parallel direction relative to the central axis C-C of the retainer body 22. The angled faces 76 are located on opposite sides 78, 88 of each of the arms. Referring to FIG. 5, the angled faces 76 have a generally convex construction in relation to the central axis C-C that defines a V-shaped profile. The faces 76 of each of the arms 34, 36 meet at an apex portion 81, which is located at a central plane P that bisects the retainer body 22.

Figure 9:
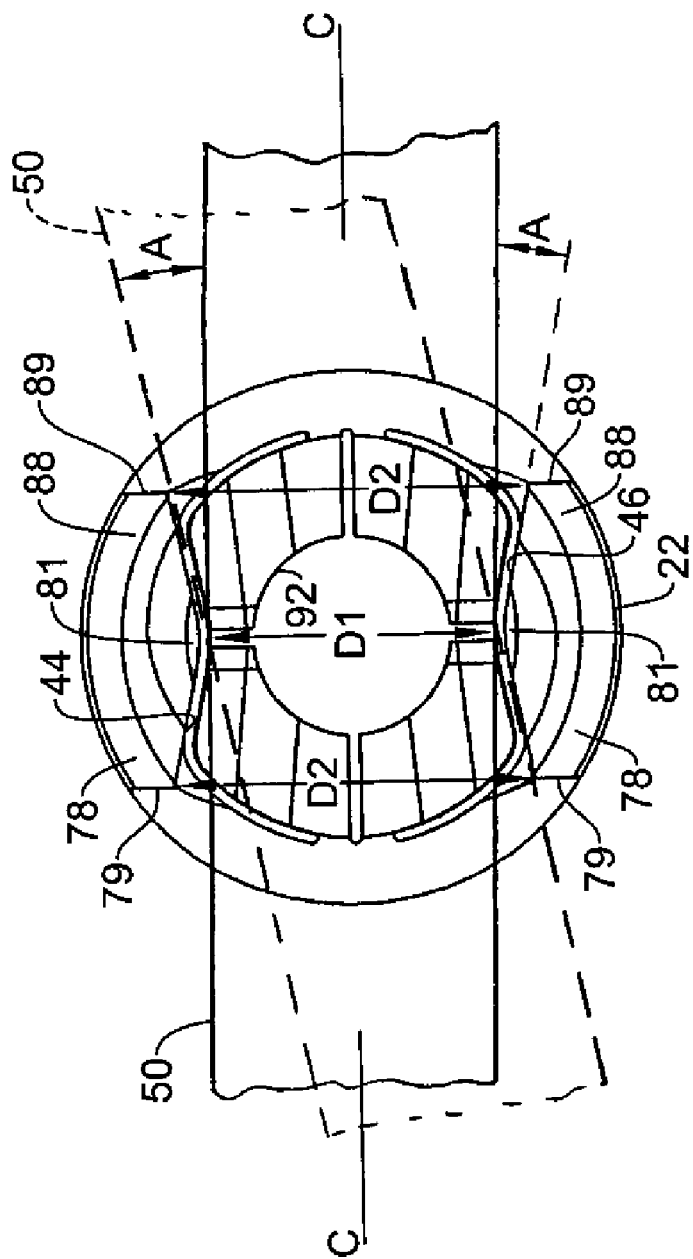
FIG. 9 is a top plan view of the retainer of FIG. 5.

Referring now to FIG. 9, a minimum distance D1 between the inner surfaces 44, 46 of the arms 34, 36 is centrally located between the sides 78, 88 of each of the arms (i.e., the minimum distance D1 is located between the apex portions 81 of the convex constructions of the arms). The minimum distance D1 generally corresponds to a diameter of the connecting rod 50. A maximum distance D2 between the inner surfaces 44, 46 is defined between edges 79, 89 of the sides 78, 88 of each of the arms 34, 36. The maximum distance D2 (due to the angled faces 76) is configured to permit angled placement of the connecting rod 50 within the first region of the retainer body 22. As can be understood, the construction of the arms 34, 36 (e.g. the minimum distance D1 and the maximum distance D2) can be modified to correspond to varying sizes of connecting rods 50.

In the illustrated embodiment, the minimum distance D1 defines a center dimension, and the maximum distance D2 between the edges of each of the arms defines first and second lateral dimensions. The center, first lateral and second lateral dimensions are generally perpendicular or transverse to the central axis C-C of the retainer 12. Preferably, the first and second lateral dimensions D2 are greater than the center dimension D1 to accommodate angled placement of a connecting rod, or to accommodate a connecting rod having a curved configuration.

In particular, the angled faces 76 of the arms 34, 36, and the subsequent dimensional construction of the first receiving region 20, is preferably configured to permit placement of a connecting rod 50 within the first receiving region 20 at a number of angular orientations relative to the central axis C-C of the retainer body 22. This arrangement facilitates ease of use of the device during a surgical procedure. For example, in some applications, the connecting rod 50 is positioned within the first receiving region 20 such that the rod is generally coaxially aligned with the central axis C-C of the retainer body 22 (shown in solid line in FIG. 9). In an alternative application, the connecting rod 50 may be angularly oriented such that the rod is angularly offset from, or non-coaxially aligned with the central axis C-C (shown in dashed lines in FIG. 9). The dimensional construction of the present retainer 12 opens up the area of the first receiving region 20 to permit a user to more easily locate or place a connecting rod 50 within the first receiving region.

Figure 10:
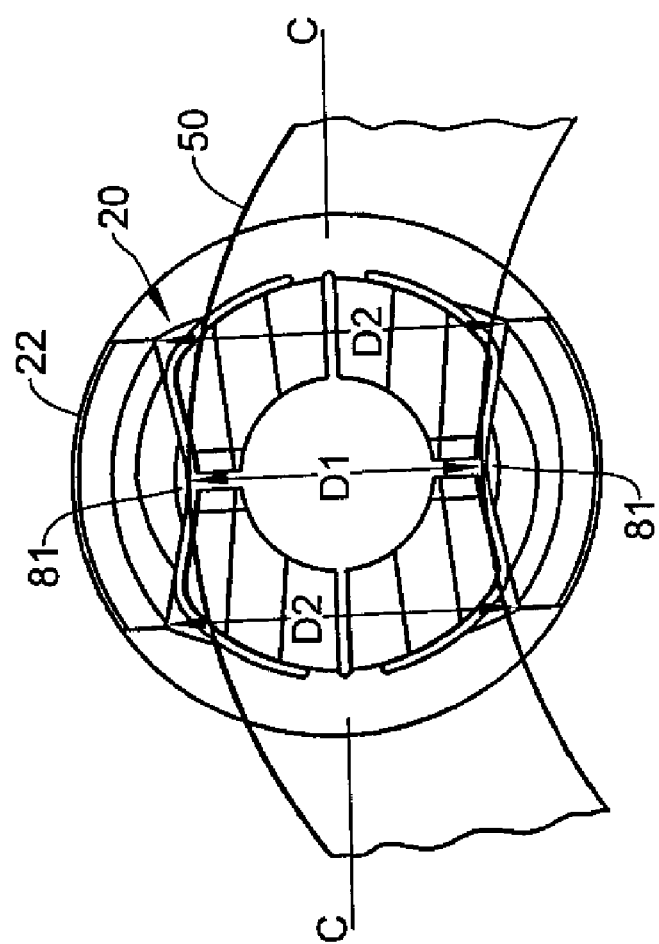
FIG. 10 is a top plan view of the retainer of FIG. 9.
Figure 11:
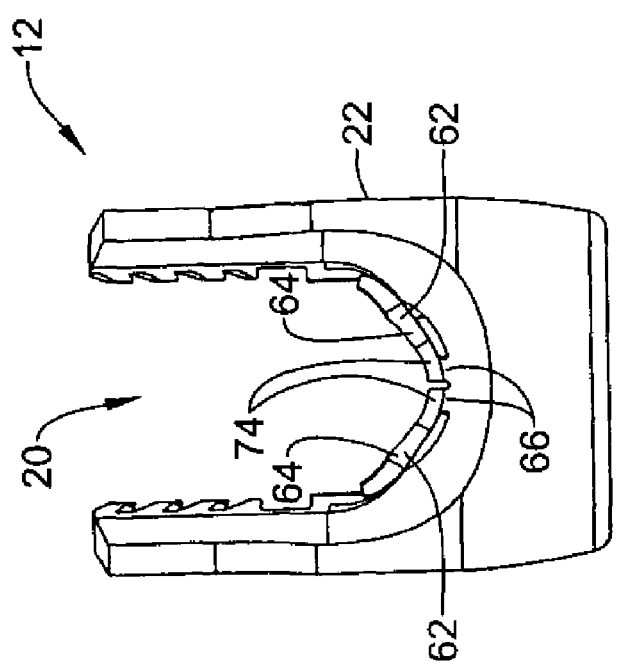
FIG. 11 is a side elevational view of the retainer of FIG. 7.

In addition, the disclosed arrangement permits a user to more easily place a connecting rod 50 having a curved or bent configuration within the first receiving region 20. Referring to FIG. 10, a bent connecting rod 50 is illustrated in a non-coaxial position within the first receiving region 20. The minimum distance D1 of the first receiving region 20 corresponds to the outer diameter of the bent connecting rod, while the maximum distance D2 accommodates the curvature of the bent connecting rod.

Referring back to FIG. 9, preferably, the arms 34, 36 are constructed to accommodate an angular offset A relative to the central axis C-C, in either direction. The term "angular offset" or "non-coaxially orientation" includes both an offset defined by a straight connecting rod oriented in a non-coaxial or non-parallel orientation relative to the central axis C-C, and an offset or non-coaxial configuration defined by the curvature of a bent connecting rod. In the illustrated embodiment, the angular offset A is preferably between 0 and 20 degrees; more preferably between about 0 and 12 degrees, in either direction relative to the central axis C-C. In other words, preferably, the first receiving region 20 has a range of 0 to 40 degrees (20 degrees in either direction) at which the connecting rod 50 may be oriented when positioned within the first receiving region 20; or more preferably, the first receiving region 20 has a range of about 0 to 24 degrees (12 degrees in either direction) at which the connecting rod 50 may be oriented.

Referring back now to FIGS. 7 and 8, the first and second arms 34, 36 each include threads 42 that engage a corresponding threaded member 40 (FIG. 2). In the illustrated embodiment, the threads 42 are internal threads formed on the inner surfaces 44, 46 of the arms 34, 36. The threaded member 40 is a corresponding set screw or plug that mates with the internal threads to secure the connecting rod 50 within the first receiving region 20 of the retainer 12. In an alternative embodiment, the threads 42 may be formed on outer surfaces 48 of the arms 34, 36, and the threaded member may include a corresponding threaded nut (not shown).

Referring again to FIGS. 6-7, the second receiving region 30 is defined within the main body portion 32 of the retainer body 22. The second receiving region 30 includes a socket or bore 52 formed at the second end 18 of the retainer body 22. The first and second receiving regions 20, 30 are separated by the intermediate structure 60 of the main body portion 32.

Figure 1:
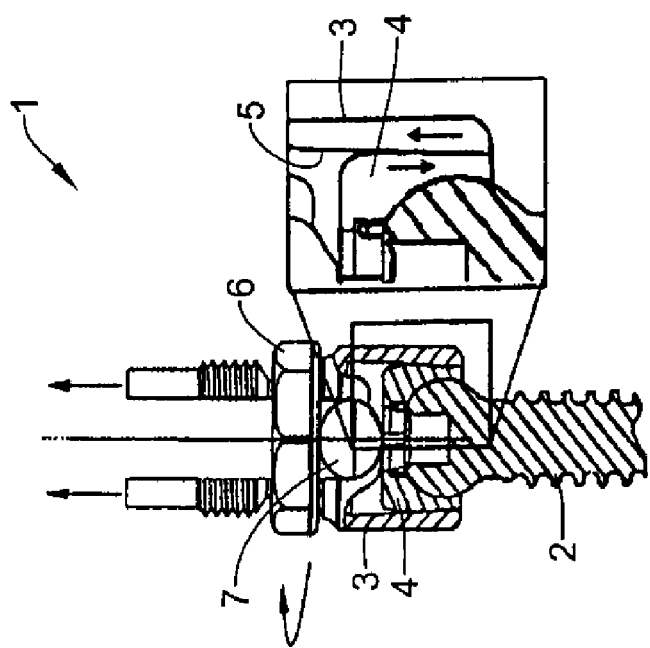
FIG. 1 is a partial cross-sectional side view of a prior art bone screw arrangement.

The intermediate structure 60 preferably includes at least one flexible element or clamping member 62. In the illustrated embodiment, four flexible elements are provided, although any number of elements can be provided in accord with the principles disclosed. The flexible elements 62 are preferably an integral construction of the main body portion 32. This eliminates the assembly costs associated with arrangements having a separate locking piece, such as the arrangement shown in FIG. 1.

Referring to FIG. 5, each of the flexible elements 62 has a free end 70 and a connected end 72. The connected end 72 of the element 62 is interconnected to the main body portion 32 of the retainer 12 at a flex location or connection region 66 (see also FIGS. 11 and 12). In the illustrated embodiment, the element 62 has a perimeter that is free or non-connected about a majority of the perimeter. That is, the flexible element 62 is spaced apart from the main body portion 32 by a gap 68 along a majority of the perimeter of the element 62. The element is thereby cantilevered from the main body portion 32 of the retainer at the connection region 66. This arrangement permits the elements 62 to flex at the connection regions 66, as will be discussed in greater detail hereinafter. The construction of the flexible elements 62 can be manufactured by, for example, an EDM process or other processes capable of creating the flexible configuration of the elements.

Figure 12:
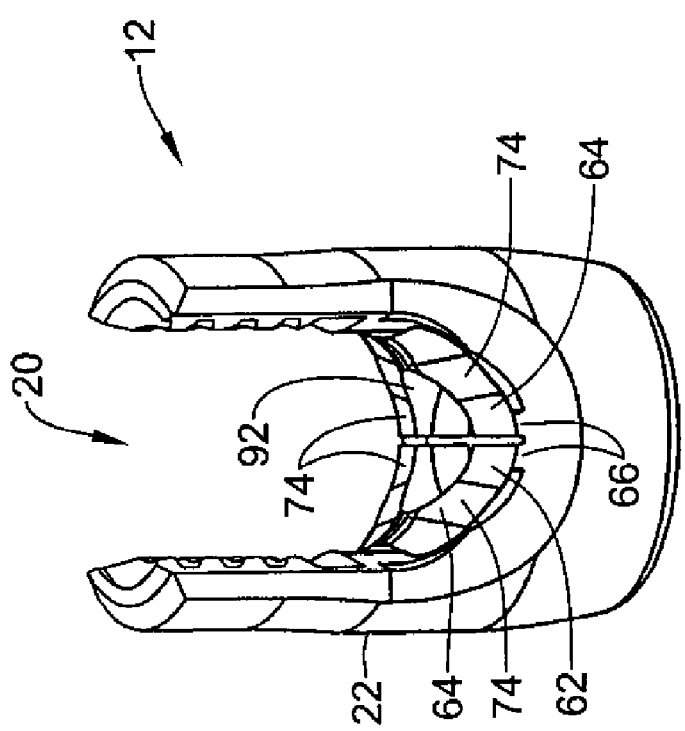
FIG. 12 is another side perspective view of the retainer of FIG. 11.
Figure 13:
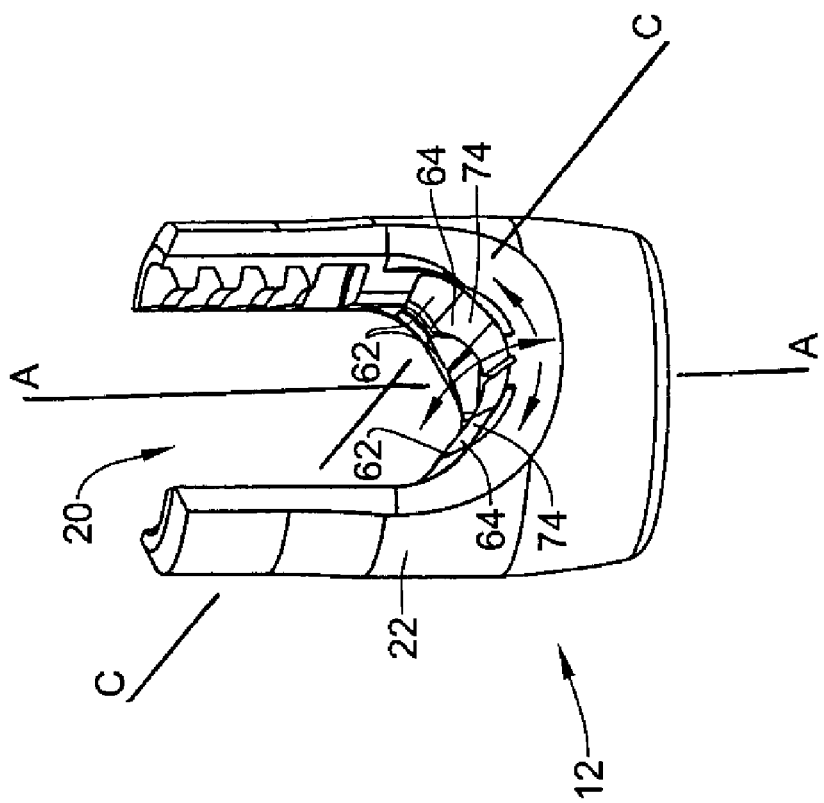
FIG. 13 is yet another side perspective view of the retainer of FIG. 12.

Referring now to FIGS. 8 and 11-13, the flexible elements 62 of the intermediate structure 60 each include a top contoured surface 74 that partially defines the first receiving region 20 of the retainer body 22. In the illustrated embodiment, the top contoured surfaces 74 of the elements 62 generally define an overall convex profile along the central axis C-C (FIG. 13). The convex profile of the top contoured surfaces 74 aids in centering a connecting rod 50 positioned within the saddle or first receiving region 20 by providing a centered contacting region at which the rod 50 naturally rests.

More specifically, the flexible elements 62 include a sloped surface 64 that crests at an opening 92 (FIGS. 12 and 8). The opening 92 is defined by a portion of the perimeter of the flexible elements 62. At the same time, the top contoured surface 74 of each of the elements are also scooped. That is, as shown in FIGS. 12 and 13, the receiving region 20 includes a convex contour that extends along the central axis C-C, and a concave contour that extends traverse to the convex contour (represented by arrows in FIG. 13). The sloped surfaces 64 and the scooped construction of the elements 62 aid in centering or aligning the connecting rod 50 in relation to the central axis C-C and the longitudinal axis A-A of the retainer 12.

Referring again to FIG. 6, stops 80 are located within the second receiving region 30 of the retainer body 22. In the illustrated embodiment, two stops 80 are oppositely located within the second receiving region 30. The stops 80 are formed on an inner wall 106 of the second receiving region 30 and project toward the center of the second receiving region 30. The stops 80 are sized and configured to contact the head 90 of the anchor 14. The stops each include at least a first tapered engagement surface 82. The tapered engagement surface 82 is configured to contact the head 90 of the anchor 14 to center the head 90 relative to the longitudinal axis A-A of the retainer 12. In the illustrated embodiment, the stops 80 include a stepped construction 83 (seen only on one side in FIG. 6) having a second tapered engagement surface 85. The stepped construction 83 and second tapered engagement surface 85 similarly guide and center the anchor 14 relative to the longitudinal axis A-A of the retainer body 22.

The stops 80 are configured to limit the axial location of the anchor 14 when positioned within the socket 52 of the retainer 12. During assembly of the bone screw arrangement 10, the anchor head 90 is positioned within the socket 52 of the second receiving region 30. A retaining ring 96 (FIG. 14) is then positioned with a groove 98 formed at the second end 18 of the retainer 12. The retaining ring 96 can be welded, bonded, or otherwise permanently or temporarily secured to the retainer 12 to capture the head 90 of the anchor 14 within the second receiving region 30.

Figure 6:
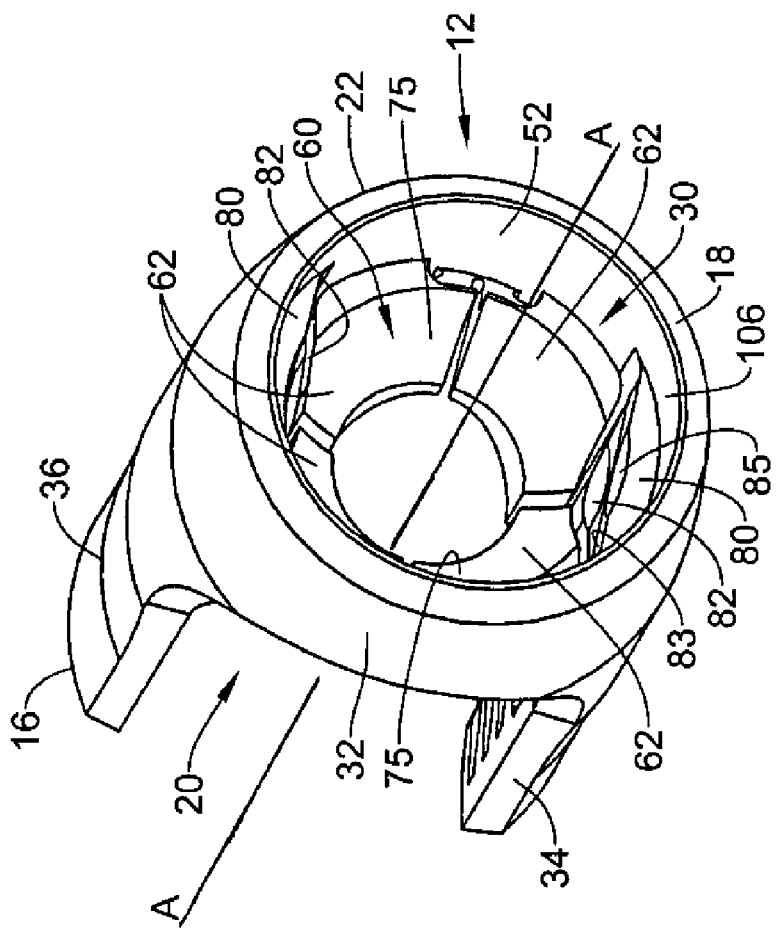
FIG. 6 is a bottom perspective view of the retainer of FIG. 5.
Figure 7:
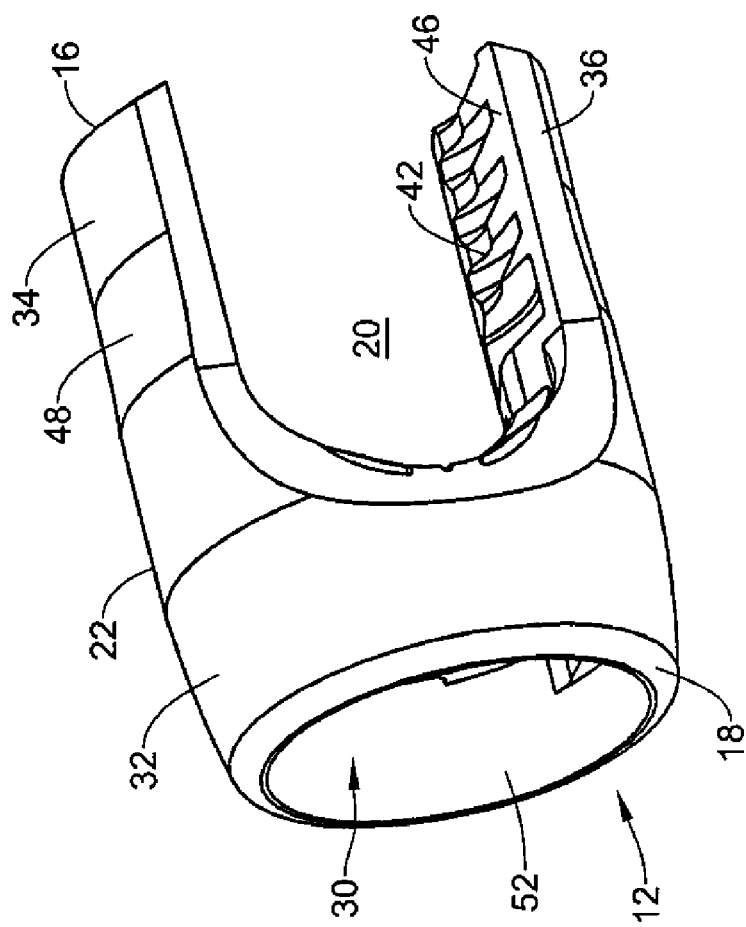
FIG. 7 is a side perspective view of the retainer of FIG. 5.
Figure 14:
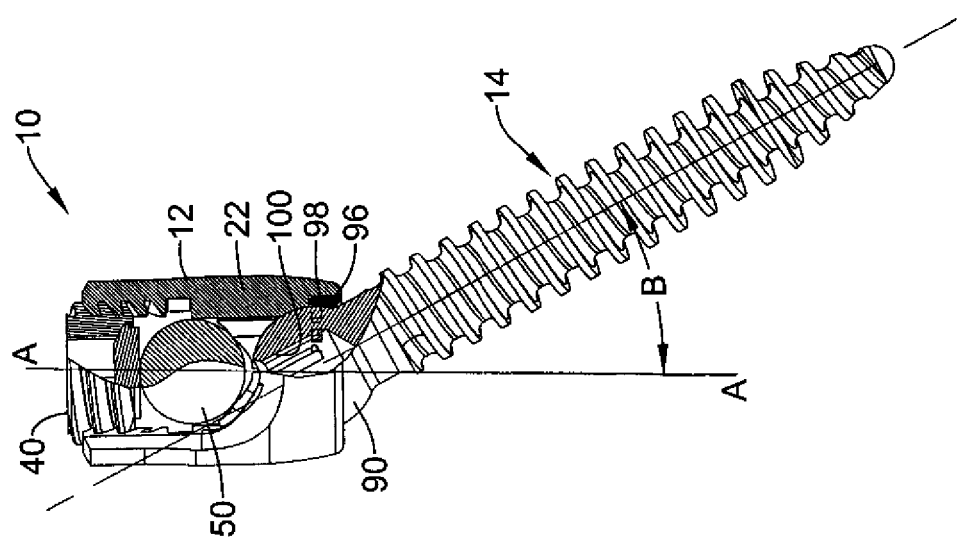
FIG. 14 is a side view, shown in partial cross-section, of the bone screw arrangement of FIG. 2.

Referring now to FIG. 14, the head 90 of the anchor 14 is generally centered with the socket 52 of the second reviving region 30 by the stops 80 (FIG. 6). In the illustrated embodiment, drive structure 100 is formed within the head 90 of the anchor 14. The drive structure 100 may include a hex construction or other type of drive structure. In use, a tool (not shown) couples to the drive structure 100 (shown in FIG. 14), which is accessed through the opening 92 (FIG. 8) of the retainer 12, to thread the anchor 14 into bone or other structure of the patient. The stops 80 aid in coaxially aligning the drive structure 100 of the anchor 14 in relation to the longitudinal axis A-A of the retainer so that the drive structure 100 of the anchor can be accessed through the opening 92. Once the anchor 14 is positioned and secured as needed, the tool is removed from the drive structure 100 of the anchor 14 and the retainer 12 can be turned to a desired orientation to receive a connecting rod 50.

In particular, the retainer body 22 can be turned (e.g. swiveled, pivoted or rotated) relative to the anchor 14 to orient the first receiving region for receipt of a connecting rod 50 (see also FIG. 2). The angled faces 76 of the arms 34, 36 provide a more open, receiving region 20 that accommodates or accepts rods having a bent configuration, or permits a user to position a straight connecting rod at a non-parallel orientation relative to the first and second arms 34, 36.

In the illustrated embodiment, the second receiving region 30 is defined by the socket and the flexible elements 62 of the intermediate structure. The elements 62 include a bottom contoured surface 75 (FIG. 6) that is generally concave in shape to at least partially define a spherically structured socket 52. The spherically structured socket 52 permits the retainer 12 and anchor 14 to freely rotate or swivel relative to one another. When the anchor 14 is secured to a structure of a patient, the retainer 12 can be turned such that a shank 102 of the anchor is positioned relative to the longitudinal axis A-A of the retainer 12 at a desired angular orientation. Preferably, the retainer can be angled at an angle B (FIG. 14) of between 0 and 50 degrees relative to the longitudinal axis A-A of the retainer 12, in any direction; more preferably between 0 and 30 degrees, in any direction. In other words, the retainer 12 and the anchor 14 preferably have a universal-type range of motion from one angled position to an opposite angled position of between 0 and 100 degrees; more preferably between 0 and 60 degrees.

After the connecting rod has been placed within the first receiving region 20, the threaded member 40 is threaded between the arms 34, 36 of the retainer 12. As the threaded member 40 is driven downward along the threads 42 formed on the arms, the connecting rod 50 begins to seat within the first receiving region 20 of the retainer 12. The connecting rod 50 centers within the first receiving region because of the scooped construction and the top contoured surfaces 74 of the flexible elements 62.

To lock all of the components (i.e. the retainer 12, the anchor 14, and the connecting rod 50) relative to one another, the user continues to assembly the bone screw arrangement by, for example, threading the threaded member 40 against the connecting rod 50 until the member 40 is tightened and fully seated. As the threaded member 40 is being tightened, the connecting rod 50 is forced against the flexible elements 62. Because of the flexible configuration of the flexible elements 62, the elements 62 are in turn, biased or forced against the head 90 of the anchor 14. The head 90 of the anchor 14 is thereby captured between the flexible elements 62 and the retaining ring 96 of the retainer 12. Each of the retainer 12, the anchor 14, and the connecting rod 50 are now in a fixed position relative to one another.

The intermediate structure 60 of the retainer eliminates the need for a separate locking piece and generally functions as an integral locking mechanism to secure all of the components in a fixed position relative to one another. By eliminating the need for a separate locking piece, the overall size and profile of the bone screw arrangement 10 is reduced to minimize the invasiveness of surgical stabilization procedures. Also, eliminating the separate locking piece reduces assembly costs, as well as sterilization costs, due to the reduced number of components.

It is to be understood that one embodiment in accord with the principles disclosed may include the configuration of the first receiving region 20, which permits placement of a connecting rod 50 at a number of non-coaxial orientations, without incorporation of the intermediate structure 60 disclosed. Likewise, another embodiment in accord with the principles disclosed may include the configuration of the flexible intermediate structure 60 without incorporation of the disclosed first receiving region 20 that permits non-coaxial orientations.

The above specification provides a complete description of the present invention. Since many embodiments of the invention can be made without departing from the spirit and scope of the invention, certain aspects of the invention reside in the claims hereinafter appended.

What is claimed is:

1. A retainer for use with a bone anchor and a connecting rod, the retainer comprising:
    a) a body having a longitudinal axis defined between a first end and a second end, the body including:
        i) a first receiving region located adjacent to the first end, the first receiving region being configured to receive a connecting rod;
        ii) a second receiving region located adjacent to the second end, the second receiving region being configured to receive a bone anchor; and
        iii) at least one flexible element integrally formed with the body and positioned between the first receiving region and the second receiving region, the flexible element having an upper surface facing the first receiving region and a lower surface facing the second receiving region, the flexible element interconnected to the body such that the flexible element is cantilevered from the body, the flexible element being configured to flex toward the second receiving region when a connecting rod is secured within the first receiving region, the upper surface being a contoured surface having a convex profile when viewed along a central axis perpendicular to the longitudinal axis and a concave profile when viewed along an axis perpendicular to both the central axis and the longitudinal axis, the contoured surface configured to guide the connecting rod toward the longitudinal axis.

2. The retainer of claim 1, wherein the first receiving region is partially defined by arms extending outward from a main portion of the body.

3. The retainer of claim 2, wherein the arms include threads for receipt of a mating threaded member to secure a connecting rod positioned within the first receiving region.

4. The retainer of claim 3, wherein the threads are internal threads.

5. The retainer of claim 3, wherein the mating threaded member is a set screw.

6. The retainer of claim 2, wherein the second receiving region is defined within the main portion of the body.

7. The retainer of claim 1, wherein the body further includes a plurality of flexible elements positioned between the first and second receiving regions of the body.

8. The retainer of claim 1, wherein the flexible element is spaced from the body along a majority of a perimeter of the element.

9. The retainer of claim 1, where in the body further includes structure formed on an inner surface of the second receiving region that centers the bone anchor relative to the longitudinal axis of the body.

10. The retainer of claim 1 wherein the body further includes a plurality of independently operating flexible elements positioned between the first and second receiving regions of the body.

11. A retainer for use with a bone anchor and a connecting rod, the retainer comprising:
    a) a main body having a longitudinal axis defined between a first end and a second end;
    b) first and second arms extending from the main body, the first and second arms defining a central axis therebetween, the central axis being generally perpendicular to the longitudinal axis of the main body; and c) a first receiving region located at the first end of the main body, and a second receiving region located at the second end of the main body;

d) wherein the first and second arms are configured to permit placement of a connecting rod having a central longitudinal axis within the first receiving region such that the central longitudinal axis of the connecting rod is positionable at a number of non-coaxial angular orientations relative to the central axis defined by the first and second arms, any two of the non-coaxial angular orientations of the central longitudinal axis of the connecting rod defining a plane that intersects the longitudinal axis of the main body at only one point.

12. The retainer of claim 11, wherein the first and second arms each include angled faces that accommodate placement of a curved connection rod within the first receiving region.

13. The retainer of claim 11, wherein the first and second arms each include angled faces that accommodate non-coaxial placement of a connection rod relative to the central axis.

14. The retainer of claim 13, wherein the angled faces are located on opposite sides of each of the arms.

15. The retainer of claim 11, wherein the central longitudinal axis of the connecting rod is angularly oriented relative to the central axis between 1 and 20 degrees.

16. The retainer of claim 11, further including an intermediate structure located between the first and second receiving regions, the intermediate structure including contoured surfaces configured to center a connecting rod in relation to the central axis when the connecting rod is positioned within the first receiving region.

17. The retainer of claim 16, wherein the intermediate structure includes at least one flexible member.

18. The retainer of claim 11, wherein each of the first and second arms include a central portion and opposite sides, the sides of the first arm being spaced apart from the sides of the second arm at a distance greater than a distance defined between the central portions of the arms.

19. A fixation device, comprising:
  a) a retainer having a longitudinal axis defined between a first end and a second end, the retainer including:
    i) a saddle region located at the first end of the retainer, the saddle region being configured to receive a connecting rod;
    ii) a socket located at the second end of the retainer; and
    iii) a flexible intermediate structure located between the saddle region and the socket, the flexible intermediate structure having an upper surface facing the saddle region and a lower surface facing the socket, the upper surface being a contoured surface facing the saddle region and configured to guide the connecting rod toward a central portion of the saddle region, the contoured surface of the upper surface comprising a convex contour when viewed along a central axis perpendicular to the longitudinal axis and a concave contour when viewed along an axis perpendicular to both the central axis and the longitudinal axis;
  b) an anchor positioned within the socket of the retainer; and
  c) a securing member positionable within the saddle region of the retainer to secure a connecting rod positioned within the saddle region;
  d) wherein each of the retainer, the anchor, and a connecting rod positioned with the saddle region of the retainer are secured in a fixed position relative to one another when the securing member seats the connecting rod within the saddle region.

20. The device of claim 19, wherein the flexible intermediate structure defines an opening to access drive structure of the anchor.

21. The device of claim 19, wherein the saddle region is defined by arms extending from a main body portion of the retainer.

22. The device of claim 21, wherein the securing member includes a set screw that forces a connecting rod positioned within the saddle region against the flexible intermediate structure.

23. The device of claim 21, wherein the first and second arms of the saddle region are configured to receive a connecting rod in a number of angular orientations relative to the first and second arms.

24. The device of claim 19, wherein the flexible intermediate structure includes a plurality of flexible elements.

25. The device of claim 24, wherein each of the elements is an integral construction of a main body portion of the retainer.

26. The device of claim 24, wherein each of the elements is spaced from a main body portion of the retainer along a majority of a perimeter of the element.

27. The device of claim 19, further including a retaining ring to retain the anchor within the socket of the retainer.

28. A method of using a bone screw arrangement, the method comprising the steps of:
  a) providing a bone screw arrangement, the bone screw arrangement including an anchor and a retainer having an integral locking structure, the retainer including a saddle region at a first end of the retainer and a socket at a second end of the retainer, the retainer including a longitudinal axis extending from the first end to the second end, the saddle region including a central axis extending perpendicular to the longitudinal axis of the retainer and bisecting the saddle region, the central axis intersecting the longitudinal axis of the retainer at a point;
  b) positioning the anchor within the socket of the retainer;
  c) pivoting the anchor to a selected axial orientation relative to the longitudinal axis of the retainer; and
  d) positioning a connecting rod within the saddle region of the retainer such that a central longitudinal axis of the connecting rod is positioned at a non-coaxial orientation relative to the central axis of the retainer, the central longitudinal axis of the connecting rod jointly defining a plane with the central axis that intersects the longitudinal axis of the retainer at the point.

29. The method of claim 28, further including biasing flexible elements of the integral locking structure against the anchor to lock the anchor in the selected axial orientation, the flexible elements being located between the saddle region and the socket.

30. The method of claim 29, wherein the step of biasing the flexible elements includes threading a threaded member to the retainer to force the connecting rod against the flexible elements such that the flexible elements are made to contact the anchor.

31. The method of claim 28, wherein the step of positioning a connecting rod includes positioning a connecting rod within the saddle region at an angle offset from the central axis, the angle being as great as 20 degrees from the central axis.

32. The method of claim 28, wherein the step of positioning a connecting rod includes positioning a curved connecting rod within the saddle region.

33. The method of claim 28, wherein the step of positioning a connecting rod includes positioning a connecting rod having a substantially curved longitudinal axis within the saddle region.

34. A retainer for use with a bone anchor and a connecting rod, the retainer comprising:
  a) a first receiving region configured to receive a connecting rod, the first receiving region including a first arm, a second arm spaced from the first arm, and a central axis extending through the first receiving region bisecting the first receiving region such that the first arm is located on a first side of the central axis and the second arm is located on a second side of the central axis opposite the first arm, each of the first and second arms including inner surfaces facing one another,
  wherein a center dimension measured across the first receiving region from the inner surface of the first arm to the inner surface of the second arm is a minimum distance between the inner surfaces of the first and second arms, the center dimension bisecting the first receiving region;
  wherein a first lateral dimension measured across the first receiving region from the inner surface of the first arm to the inner surface of the second arm is greater than the center dimension;
  wherein a second lateral dimension measured across the first receiving region from the inner surface of the first arm to the inner surface of the second arm is greater than the center dimension;
  wherein each of the first lateral dimension and the second lateral dimension is parallel to the center dimension, and wherein the center dimension is located between the first lateral dimension and the second lateral dimension;
  wherein each of the center dimension, the first lateral dimension and the second lateral dimension are perpendicular to the central axis; and
  b) a second receiving region configured to receive a bone anchor.

35. The retainer of claim 34, wherein the inner surfaces of each of the first and second arms each include a centrally located apex, wherein the center dimension is measured across the first receiving region from the apex of the inner surface of the first arm to the apex of the inner surface of the second arm.

36. The retainer of claim 35, wherein the inner surfaces of each of the first and second arms each include a plurality of angled faces that meet at the respective apex.

37. A bone fixation device for use with a connecting rod, the bone fixation device comprising:
  a) a yoke having an upper pocket for receiving a connecting rod and a lower socket;
  b) a bone anchor including a head mounted in the lower socket of the yoke; and
  c) a plurality of clamping members having upper surfaces that define a portion of the upper pocket and lower surfaces that define a portion of the lower socket, the clamping members being integrally connected with the yoke at flex locations, and the clamping members being configured to directly clamp the head of the bone anchor within the lower socket when the connecting rod is secured within the upper pocket.

* * * * *